United States Patent
Wang et al.

(10) Patent No.: US 9,972,228 B2
(45) Date of Patent: May 15, 2018

(54) ANNULAR MULTI-SURFACE DISPLAY DEVICE

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Jiaheng Wang, Beijing (CN); Feng Bai, Beijing (CN); Jiuxia Yang, Beijing (CN); Jiantao Liu, Beijing (CN)

(73) Assignees: BOE Technology Group Co., Ltd., Beijing (CN); Beijing BOE Optoelectronics Technology Co., Ltd., Beijing (CN)

( * ) Notice: Subject to any disclaimer, the term of this patent is extended or adjusted under 35 U.S.C. 154(b) by 90 days.

(21) Appl. No.: 14/893,289

(22) PCT Filed: Jun. 19, 2015

(86) PCT No.: PCT/CN2015/081916
§ 371 (c)(1),
(2) Date: Nov. 23, 2015

(87) PCT Pub. No.: WO2016/090891
PCT Pub. Date: Jun. 16, 2016

(65) Prior Publication Data
US 2016/0329003 A1    Nov. 10, 2016

(30) Foreign Application Priority Data
Dec. 12, 2014  (CN) .......................... 2014 1 0773840

(51) Int. Cl.
*G09G 5/00*         (2006.01)
*G09F 9/30*         (2006.01)
(Continued)

(52) U.S. Cl.
CPC ............ *G09F 9/301* (2013.01); *A61B 5/0075* (2013.01); *A61B 5/01* (2013.01); *A61B 5/14532* (2013.01);
(Continued)

(58) Field of Classification Search
None
See application file for complete search history.

(56) References Cited

U.S. PATENT DOCUMENTS

2004/0150329 A1* 8/2004 Asai .................... H01L 51/5275
                                                    313/506
2007/0033847 A1   2/2007 Tanaka
(Continued)

FOREIGN PATENT DOCUMENTS

CN         1912727 A      2/2007
CN       201181385 Y      1/2009
(Continued)

OTHER PUBLICATIONS

Chinese Office Action in Chinese Application No. 201410773840.1 dated Jun. 3, 2016 with English translation.
(Continued)

*Primary Examiner* — Ifedayo Iluyomade
(74) *Attorney, Agent, or Firm* — Collard & Roe, P.C.

(57) ABSTRACT

An annular multi-surface display device includes: a display panel, with two opposite sides of the display panel being bent toward a back surface of a display area respectively and being sealed together, so that a cross section of the display panel which is obtained along a direction perpendicular to the two opposite sides forms a closed annular structure; where an outer surface of the display panel with the cross section being the closed annular structure is a tubular surface, and a display surface of the annular multi-surface display device is the outer surface of the display panel.

18 Claims, 3 Drawing Sheets

(51) Int. Cl.
  *G09F 9/00*    (2006.01)
  *A61B 5/00*    (2006.01)
  *A61B 5/01*    (2006.01)
  *A61B 5/145*   (2006.01)
  *G09F 9/302*   (2006.01)
  *G09G 5/14*    (2006.01)
  *H04N 5/225*   (2006.01)
  *G06F 3/147*   (2006.01)

(52) U.S. Cl.
  CPC .............. *G06F 3/147* (2013.01); *G09F 9/00* (2013.01); *G09F 9/302* (2013.01); *G09G 5/14* (2013.01); *H04N 5/2253* (2013.01); *H04N 5/2257* (2013.01); *A61B 5/7445* (2013.01); *G09G 2380/02* (2013.01)

(56) References Cited

U.S. PATENT DOCUMENTS

| | | | |
|---|---|---|---|
| 2009/0096965 | A1 | 4/2009 | Nagata |
| 2010/0238366 | A1 | 9/2010 | Chang et al. |
| 2012/0038602 | A1 | 2/2012 | Lee et al. |
| 2014/0327954 | A1* | 11/2014 | Hsu ................. G02F 1/167 359/296 |
| 2015/0070475 | A1* | 3/2015 | Kim ................. G02B 27/2278 348/51 |
| 2016/0029896 | A1* | 2/2016 | Lee .................. A61B 5/01 600/474 |

FOREIGN PATENT DOCUMENTS

| | | | |
|---|---|---|---|
| CN | 202178837 U | 3/2012 | |
| CN | 202634562 U | 12/2012 | |
| CN | 103279260 A | 9/2013 | |
| CN | 103393414 A | 11/2013 | |
| CN | 203573577 U | 4/2014 | |
| CN | 104143291 A | 11/2014 | |
| CN | 104199544 A | 12/2014 | |
| CN | 104392668 A | 3/2015 | |
| CN | 104424856 A | 3/2015 | |
| CN | 204242526 U | 4/2015 | |
| DE | 100 00 468 A1 | 7/2001 | |
| KR | 20140098488 | * 7/2014 | ............... A61B 5/01 |

OTHER PUBLICATIONS

Second Chinese Office Action in Chinese Application No. 201410773840.1 dated Dec. 8, 2016 with English translation.

International Search Report of PCT/CN2015/081916 in Chinese, dated Sep. 14, 2015 with English translation.

Notice of Transmittal of the International Search Report of PCT/CN2015/081916 in Chinese, dated Sep. 14, 2015.

Written Opinion of the International Searching Authority of PCT/CN2015/081916 in Chinese, dated Sep. 14, 2015 with English translation.

Hiroaki, Kitahara. "[SID] Borderless! Sharp releases panel of 'flexible design'", http://china.nikkeibp.com.cn/news/auto/70896-201406091651.html, retrieved May 10, 2016, in Chinese with English translation.

Tanaka, Naoki, "Success of Sharp's small and medium-sized LCD panel business depends on performance of IGZO", Nikkei electronics, http://china.nikkeibp.com.cn/news/flat/71297-201407081545.html, retrieved May 10, 2016, in Chinese with English translation.

* cited by examiner

ANNULAR MULTI-SURFACE DISPLAY DEVICE

CROSS REFERENCE TO RELATED APPLICATIONS

This application is the National Stage of PCT/CN2015/081916 filed on Jun. 19, 2015, which claims priority under 35 U.S.C. § 119 of Chinese Application No. 201410773840.1 filed on Dec. 12, 2014, the disclosure of which is incorporated by reference.

TECHNICAL FIELD

Embodiments of the present disclosure relates to an annular multi-surface display device.

BACKGROUND

With an expansion of an application field of display devices, utilization of display devices is not limited to flat panel displays. Nowadays, design of devices capable of displaying in multiple surfaces has already emerged. This type of multi-surface display devices is generally formed by joining a plurality of flat display screens together to form a closed square column structure to display in each direction of the square column structure respectively. For example, similar to a design of a light box, images displayed on each surface of this type of multi-surface display devices are relatively independent, and there are angular corners on the joints of the display surfaces. Thus, this type of multi-surface display devices cannot achieve display continuity of images in each direction.

SUMMARY

Embodiments of the present disclosure provide an annular multi-surface display device that includes: a display panel, with two opposite sides of the display panel being bent toward a back surface of a display area respectively and being sealed together so that a cross section of the display panel which is obtained along a direction perpendicular to the two opposite sides forms a closed annular structure; where an outer surface of the display panel with the cross section being the closed annular structure is a tubular surface, and a display surface of the annular multi-surface display device is the outer surface of the display panel.

BRIEF DESCRIPTION OF THE DRAWINGS

In order to clearly illustrate the technical solution of the embodiments of the disclosure, the drawings of the embodiments will be briefly described in the following; it is obvious that the described drawings are only related to some embodiments of the disclosure and thus are not limitative of the disclosure.

DETAILED DESCRIPTION

Figure 1:
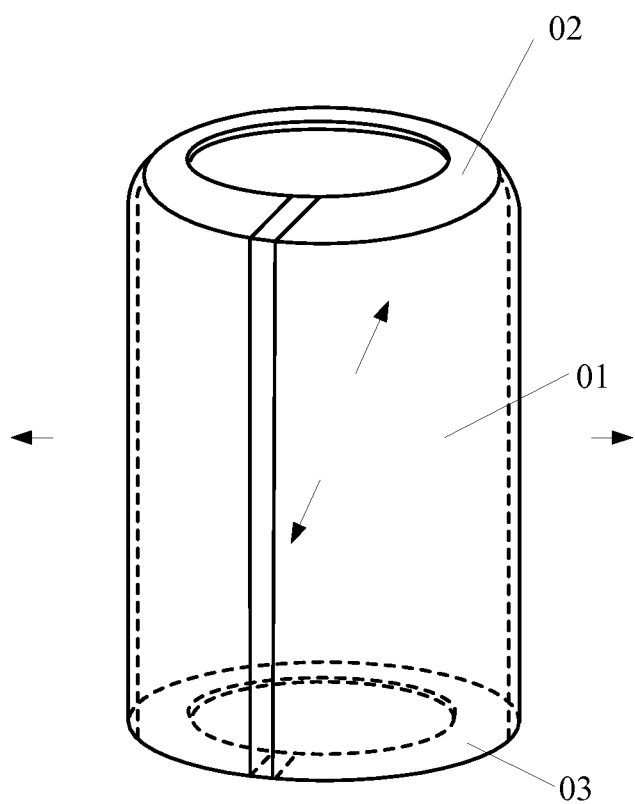
FIG. 1 is a first stereoscopic schematic view of an annular multi-surface display device according to an embodiment of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

The detailed description of the annular multi-surface display device according to embodiments of the present disclosure will be described below in details with reference to the drawings.

Shapes and sizes of each component in the drawings do not reflect the actual ratios of the annular multi-surface display device, and only serve to illustrate the content of the present disclosure by way of examples.

An annular multi-surface display device according to an embodiment of the present disclosure, as shown in FIG. 1, includes: a display panel 01 with two opposite sides being bent toward the back surface of the display area respectively to form an annular structure. That is to say, the two opposite sides of the display panel are bent toward the back surface of the display area respectively and being sealed or jointed together, so as to make a cross section of the display panel obtained along a direction perpendicular to the two opposite sides to form a closed annular structure. For example, before bending the display panel and sealing or joining the two sides together, the display panel is of a rectangular shape. For example, the back surface of the display area refers to a surface opposite to a display surface of the display panel herein.

Figure 2:
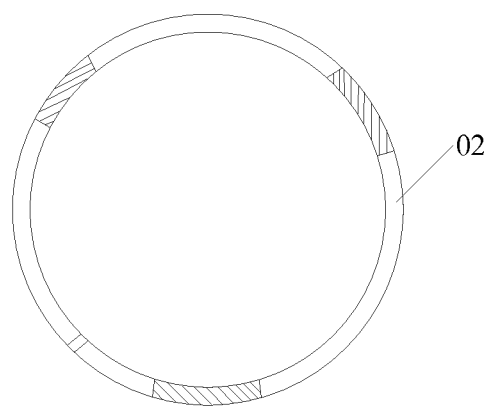
FIG. 2 is a top schematic view of an annular multi-surface display device according to an embodiment of the present disclosure.

The sealing of the two sides of the display panel 01 which are bent toward the back surface of the display area enables the display panel 01 to form an exterior side surface (an outer surface), which is a curved and closed annular structure. That is, the outer surface of the display panel forms a tubular surface. For example, the tubular surface formed by the outer surface is smooth without any ridges. As shown in FIG. 2 which is the top schematic view and FIG. 3 which is the bottom schematic view, the display surface of the annular multi-surface display device is the exterior side surface (the outer surface) of the closed annular structure.

The above-mentioned annular multi-surface display device provided in an embodiment of the present disclosure provides a display panel which is bent into an annular structure to be sealed as a closed annular structure, and surfaces in each direction of the closed annular structure can implement the function of displaying images; and application of the display panel which is bent into an annular structure can achieve that the display surfaces in each direction are circular curved surfaces and without any angular corners or ridges. Compared with a multi-surface display with multiple ridges and formed by a plurality of display panels with flat surfaces, the display panel described herein can improve the continuity of the display images in each direction of the multi-surface display device.

The annular multi-surface display device mentioned above according to an embodiment of the present disclosure provides a display panel 01 which is bent into an annular structure to be sealed as a closed annular structure. It can be seen from FIG. 1 that surfaces in each direction of the closed annular structure are circular curved surfaces and can display images; and due to application of the structure which is bent into a ring, the display surfaces in each direction of the display panel 01 are circular curved surfaces and without any angular corners. Compared with an existing multi-surface display formed by a plurality of flat display panels, the existing multi-surface display has a plurality of angular corners. However, the display device according to an embodiment of the present disclosure can display images continuously in each direction.

It should be noted that, for the convenience of the description in the following, as shown in FIG. 1, an oblique arrow that points upward is used to illustrate a rear surface of the closed annular structure (e.g., an outer surface on a side that is away from a reader), an oblique arrow that points downward is used to illustrate a front surface of the closed annular structure (e.g., an outer surface on a side that is close to the reader), an arrow pointing to the left is used to illustrate a left surface of the closed annular structure, and an arrow pointing to the right is used to illustrate a right surface of the closed annular structure.

For example, a shape of a cross section of the closed annular structure can be adjusted according to application scenarios of the annular multi-surface display device, so that an outer shape of the closed annular structure is close to or similar to a tubular structure with a circular cross section or a tubular structure with an oval cross section. When applying the annular multi-surface display device to a mobile terminal such as a mobile phone for displaying images, the front surface and the rear surface of the multi-surface display device can be provided with a larger area, and the left surface and the right surface can be provided with a narrower area. For example, a major axis of the oval cross section of the closed annular structure is much longer than a minor axis of the oval cross section to facilitate an ultra-thin design of the mobile terminal. Furthermore, components such as a power supply component and a circuit board that are required in a mobile terminal can be disposed inside the closed structure of the annular multi-surface display device, so that an outer surface of the mobile terminal can be formed as a whole to display images. When applying the annular multi-surface display device to a stereoscopic multi-surface display such as a stereoscopic display wall, the front surface, the rear surface, the left surface and the right surface of the multi-surface display device can be configured to have an approximately equal area. For example, the cross section of the closed annular structure is approximately in a circular shape. Similar description will not be repeated here.

For example, in the annular multi-surface display device mentioned above according to an embodiment of the present disclosure, at least one display surface can be set as a main display surface according to the application scenarios of the annular multi-surface display device. For example, when the annular multi-surface display device is applied in the mobile phones, the front surface and the rear surface can be set as main display surfaces, and operating states of the annular multi-surface display device can be set as follows:

1. the main display surfaces can display the same content at the same time; for example, the front surface and the rear surface can display the same image at the same time;

2. a plurality of main display surfaces can display different contents respectively; for example, the front surface displays a front image of a human body, and the rear surface displays a back image of a human body; and 3. only one of the main display surfaces displays content, and the other main display surfaces are in a shut-off state.

In addition, in the above-mentioned annular multi-surface display device provided in embodiments of the disclosure, some user interface (UI) icons such as function keys or APP software icons can be configured in other display surfaces other than the main display surfaces according to actual needs. For example, function buttons can be displayed on the left surface and/or the right surface of the annular multi-surface display.

The settings and operating states of the main display surfaces are illustrated by way of examples. For example, the display panel 01 can also be treated as a whole for displaying the same content, or displaying different contents in different areas, which is not limited here.

For example, in the annular multi-surface display device mentioned above according to an embodiment of the present disclosure, the display panel 01 can be manufactured using a touch display panel to facilitate users to perform corresponding operations directly on the display panel 01 when function keys are displayed on the display panel 01. Of course, the display panel 01 can also include a non-touch display panel, which is not limited here.

Furthermore, when the annular multi-surface display device is applied in display walls, the display panel can also be manufactured as a transparent display panel, so that some items can be disposed inside the closed annular structure formed by the display panel 01 as exhibition. The corresponding display panel 01 can display relevant information such as introduction content of the exhibited items, which can be browsed through using the touch function of the annular multi-surface display device. When the annular multi-surface display device is applied in a mobile phone, the display panel is generally set as an opaque display panel.

For example, in the annular multi-surface display device mentioned above according to an embodiment of the present disclosure, the display panel 01 can be, for example, a liquid crystal display panel, an organic light-emitting diode display panel or an electronic paper display panel.

Furthermore, because the display panel 01 needs to be bent, a flexible substrate can be selected to manufacture the display panel 01. The flexible substrate includes a glass substrate, and materials for corresponding functional films also needs to have appropriate flexibility, so as to ensure that the display panel 01 can be bent to a certain extent.

For example, when manufacturing the annular multi-surface display device mentioned above according to an embodiment of the present disclosure, in order to seal the display panel 01 which is bent into the annular structure into a closed annular structure, the sealing sides of the display panel can be sealed through various ways. For example, the various sealing ways include an approach of pressing together grooves and corresponding projections that match each other, an approach of gluing the two sealing sides together, an approach of using screws to connect the two sealing sides together, or an approach of setting an independent sealing board to connect the two sealing sides together. No limitation is placed herein.

For example, when the display panel 01 is sealed through the above-mentioned approach of pressing the grooves and the corresponding projections together or gluing the two sealing sides together, a seal in the display panel 01 can be implemented without using frames. That is, during manufacture of the display panel 01, the left side and the right side of the display panel 01 can be configured without any frames, so that the display panel 01 can be frame-free at least at the sealing area to ensure a frameless effect on the sealing area of the display panel 01.

For example, the display panel 01 generally also includes a circuit board. In order to ensure connection between the circuit board and the display area of the display panel, the two can also be connected with each other through a flexible electronic skin. The flexible electronic skin generally can be made from rubber mesh conductive material. When the display area and the circuit board are connected through the flexible electronic skin, the four edges of the display panel 01 are all packaged without frames, and the ultimate assembled annular multi-surface display device can achieve real frameless annular display.

Figure 4A:
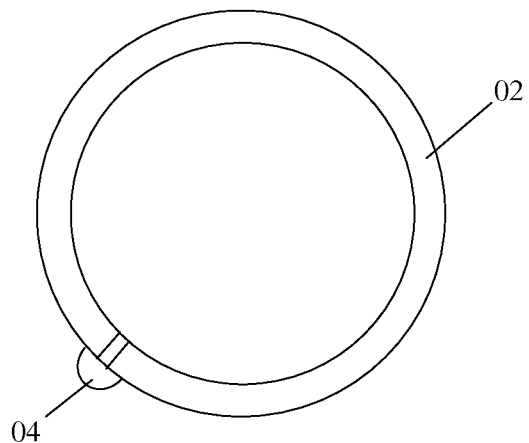
FIG. 4*a* is a first schematic view of an annular multi-surface display device provided with a transparent prism structure according to an embodiment of the present disclosure.

For example, in the annular multi-surface display device mentioned above according to an embodiment of the present disclosure, an optical design can be added to make a sealing frame of the display panel 01 to be invisible to a viewer visually. For example, as shown in FIG. 4a, a transparent prism structure 04 which is used for changing a propagation direction of an outgoing light can be manufactured on the sealing area of the display panel 01. The transparent prism structure 04 can refract the light which originally emits toward the right front of the sealing area of the display panel 01 to the sealing area, so as to make the viewer not to notice the seam visually to achieve a visually frameless annular display. For example, the transparent prism structure 04 covers a connection area (e.g., the seam) of the two opposite sides and part of the areas that surround the connection area, so that the light from the surrounding areas of the seam can be refracted to a location of the seam such that the viewer can not see the seam.

It should be noted that, when manufacturing the display panel using the organic light-emitting diode display panel, the thin film encapsulation technology of the organic light-emitting diode display panel can be used to physically achieve frame-free display. However, when manufacturing the display panel using the liquid crystal display panel or the electronic paper display panel, due to limitations on the sealing technology of the liquid crystal display panel and the electronic paper display panel, a physically frameless display panel cannot be achieved, and therefore some optical designs (e.g., transparent prism structures) are needed to achieve the optical frameless effect. Of course, when manufacturing the display panel using the organic light-emitting diode display panel, some optical designs can also be used to optimize the frame-free effect.

Figure 4B:
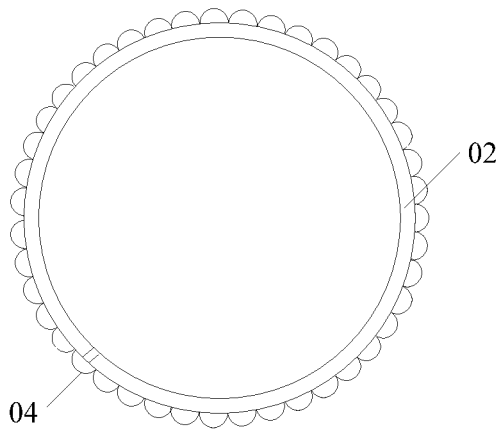
FIG. 4*b* is a second schematic view of an annular multi-surface display device provided with transparent prism structures according to an embodiment of the present disclosure.

For example, as shown in FIG. 4a, it can be possible to dispose a transparent prism structure 04 only at the sealing area of the display panel 01; alternatively, as shown in the FIG. 4b, the whole outer surface of the display panel 01 can be disposed with transparent prism structures 04. No limitation is placed herein.

Figure 5:
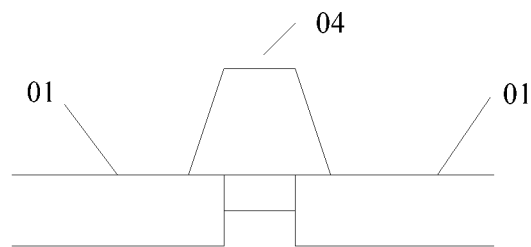
FIG. 5 is a third schematic view of an annular multi-surface display device provided with a transparent prism structure according to an embodiment of the present disclosure.

Furthermore, at least part of the transparent prism structure 04 disposed on the sealing area of the display panel 01 protrudes from the closed annular structure (e.g., the outer surface of the display panel 01), as shown in the cross-sectional view in FIG. 5. And, a cross section of the transparent prism structure 04 which is perpendicular to an outer surface of the closed annular structure (e.g., an outer surface of the display panel 01) can be set as a semicircular shape (illustrated in FIGS. 4a and 4b) or a trapezoid shape (illustrated in FIG. 5) or other shapes to change a propagation direction of the outgoing light.

For example, in the annular multi-surface display device mentioned above according to an embodiment of the present disclosure, as shown in FIG. 1, an upper edge 02 of the display panel 01 can also be bent toward the back surface of the display area to form a certain angle between the upper edge 02 and the outer surface of the closed annular structure formed by the display panel 01, and the angle can generally be a right angle; and/or a lower edge 03 of the display panel 01 is bent toward the back surface of the display area to form a certain angle between the lower edge 03 and the outer surface of the closed annular structure formed by the display panel 01, and the angle can generally be a right angle.

After the upper edge 02 and/or the lower edge 03 of the display panel 01 are bent inward, some components such as physical function keys and/or function grooves can be disposed on the upper edge 02 and/or the lower edge 03, so as to make the outer surface of the annular multi-surface display device to serve as a whole display to facilitate implementation of seamless annular display.

Figure 3:
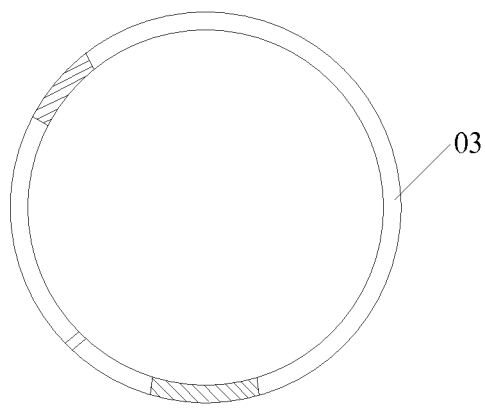
FIG. 3 is a bottom schematic view of an annular multi-surface display device according to an embodiment of the present disclosure.

For example, the annular multi-surface display device mentioned above according to an embodiment of the present disclosure, as shown in FIG. 2 and FIG. 3, further includes: at least one function groove and/or a physical function key; for example, the function groove can be a secure digital (SD) card slot, a subscriber identity module (SIM) card slot, a universal serial bus (USB) insertion slot, a headset slot and/or a charging slot, etc.; the physical function key can be a switch button, a volume adjusting button or a brightness adjustment button, etc. When the annular multi-surface display device mentioned above according to an embodiment of the present disclosure are provided with frames on its left side and right side, the function groove and/or physical function key can be disposed on the sealing area of the display panel 01, and/or disposed on the non-display area of the display panel 01. When there is no frame on the annular multi-surface display device mentioned above according to an embodiment of the present disclosure, the function groove and/or the physical function key can be disposed on the bent upper edge 02 and/or the bent lower edge 03 of the display panel 01, and/or disposed on an inner surface of the closed annular structure formed by the display panel. FIG. 2 shows three function grooves on the bent upper edge 02 of the display panel 01, and FIG. 3 shows two physical function keys on the bent lower edge 03 of the display panel 01.

For example, besides providing a function of displaying in multiple surfaces, the annular multi-surface display device mentioned above according to an embodiment of the present disclosure can be added with some other functions to increase a value of a related product. For example, the annular multi-surface display device mentioned above according to an embodiment of the present disclosure further includes: a health monitoring unit; the health monitoring unit can detect a health status of a human body, and can also implement telemedicine, and can display correspondingly on the display surface of the annular multi-surface display device.

When the annular multi-surface display device mentioned above according to an embodiment of the present disclosure are provided with frames on its left side and right side, the health monitoring unit can be disposed on the sealing area of the display panel 01 and/or on the non-display area of the display panel 01; when there is no frame on the annular multi-surface display device mentioned above according to an embodiment of the present disclosure, the health monitoring unit can be disposed on the bent upper edge 02 and/or the bent lower edge 03 of the display panel 01, and can also be disposed in an inner surface of the closed annular structure formed by the display panel.

Generally, the health monitoring unit includes a data acquisition unit, and a data analysis and storage unit. For example, infrared sampling or sensor sampling is generally used in the data acquisition unit. For example, the health monitoring unit can include an infrared detection unit and/or a minimally invasive detection unit; the infrared detection unit can be used for monitoring a body temperature; and the minimally invasive detection unit can be used for monitoring a blood sugar level.

Figure 6:
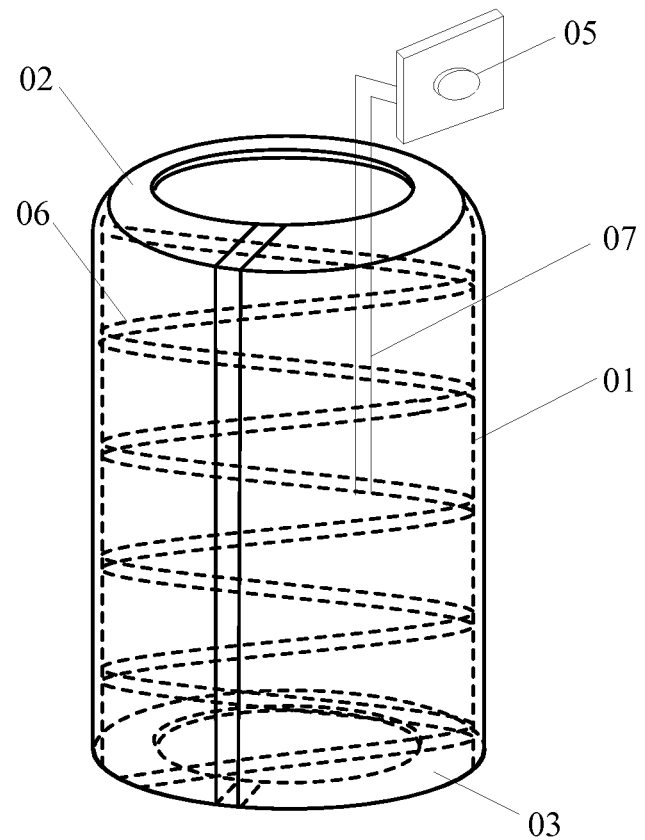
FIG. 6 is a second stereoscopic schematic view of an annular multi-surface display device according to an embodiment of the present disclosure.

For example, the annular multi-surface display device mentioned above according to an embodiment of the present disclosure can also be provided with a function of image acquisition. For example, as shown in FIG. 6, the annular multi-surface display device further includes: a camera device 05, a sliding slot 06 disposed on an inner surface of the closed annular structure formed by the display panel 01, a support member 07 for supporting a rotation of the camera device 05 or a sliding of the camera device 05 along the sliding slot 06, and a control chip (not shown in FIG. 6) for controlling movement of the support member 07 to enable the camera device 05 to capture images outside the closed annular structure formed by the display panel 01. A 360-degree image acquisition outside the annular multi-surface display device can be achieved through the interaction of the sliding slot 06, the support member 07 and the camera device 05, and the acquired images can be displayed by the annular multi-surface display device in real time.

For example, in the annular multi-surface display device mentioned above, the arrangement of the sliding slot 06 in the closed annular structure can be in various ways. For example, as shown in FIG. 6, the sliding slot 06 can be configured as a sliding slot that spirally ascends along the inner surface of the closed annular structure. No limitation is placed herein.

The annular multi-surface display device according to an embodiment of the present disclosure includes a display panel with two opposite sides being bent toward a back surface of the display area respectively to form an annular structure. The two sides of the display panel, which are bent to the back surface of the display area, can be sealed to form a closed annular structure with a curved outer surface; a display surface of the annular multi-surface display device is the outer surface of the closed annular structure. The above-mentioned annular multi-surface display device provided in an embodiment of the present disclosure provides a display panel which is bent into an annular structure to be sealed as a closed annular structure, and surfaces in each direction of the closed annular structure can be used to implement the function of displaying images; and due to application of the display panel being bent into an annular structure, the display surfaces of the display panel in each direction are circular curved surfaces and without any angular corners. Compared with an existing multi-surface display formed by a plurality of flat display panels, the existing multi-surface display has a plurality of angular corners. However, the display device according to an embodiment of the present disclosure can display images continuously in each direction.

What are described above is related to the illustrative embodiments of the disclosure only and not limitative to the scope of the disclosure; the scopes of the disclosure are defined by the accompanying claims.

The present application claims the priority of the Chinese Patent Application No. 201410773840.1 filed on Dec. 12, 2014, which is incorporated herein in its entirety by reference as part of the disclosure of the present application.

The invention claimed is:

1. An annular multi-surface display device, comprising: a display panel, with two opposite sides of the display panel being bent toward a back surface of a display area respectively and being sealed together, so that a cross section of the display panel which is obtained along a direction perpendicular to the two opposite sides forms a closed annular structure; wherein an outer surface of the display panel with the cross section being the closed annular structure is a tubular surface, and a display surface of the annular multi-surface display device is the outer surface of the display panel; wherein the display panel is provided with a transparent prism structure at least on the sealing area, and the transparent prism structure is used for changing a propagation direction of an outgoing light, wherein an upper edge of the display panel is located at one end of the two opposite sides of the display panel which are bent toward the back surface of the display area, and a certain angle is formed between the upper edge and the outer surface of the display panel; and a lower edge of the display panel is located at another end of the two opposite sides of the display panel which are bent toward the back surface of the display area, and another certain angle is formed between the lower edge and the outer surface of the display panel.

2. The annular multi-surface display device according to claim 1, wherein the two opposite sides of the display panel are sealed together through an approach of pressing together grooves and corresponding projections that match each other, an approach of gluing the two sides together, an approach of using screws to connect the two sides together, or an approach of using a sealing board to seal the two sides together.

3. The annular multi-surface display device according to claim 1, further comprising: at least one function groove and/or a physical function key; wherein:
   the function groove and/or the physical function key are disposed on a sealing area of the display panel; or
   the function groove and/or the physical function key are disposed on a non-display area of the display panel; or
   the function groove and/or the physical function key are disposed on the bent upper edge and/or the bent lower edge of the display panel; or
   the function groove and/or the physical function key are disposed on an inner surface of the display panel that is opposite to the outer surface of the display panel.

4. The annular multi-surface display device according to claim 1, further comprising: a health monitoring unit; wherein:
   the health monitoring unit is disposed on the sealing area; or
   the health monitoring unit is disposed on a non-display area of the display panel; or
   the health monitoring unit is disposed on the bent upper edge and/or the bent lower edge of the display panel; or
   the health monitoring unit is disposed on an inner surface of the display panel that is opposite to the outer surface of the display panel.

5. The annular multi-surface display device according to claim 4, wherein the health monitoring unit includes an infrared detection unit and/or a minimally invasive detection unit; wherein:
the infrared detection unit is configured for monitoring a body temperature; and
the minimally invasive detection unit is configured for monitoring a blood sugar level.

6. The annular multi-surface display device according to claim 1, wherein the display panel is frameless at least on the sealing area.

7. The annular multi-surface display device according to claim 1, wherein the display panel further comprises a circuit board, the circuit board and the display panel are connected with each other through a flexible electronic skin.

8. The annular multi-surface display device according to claim 1, wherein at least part of the transparent prism structure protrudes from the outer surface of the display panel; and a cross section of the transparent prism structure, which is perpendicular to the outer surface of the display panel, is of a semicircular shape or a trapezoid shape.

9. The annular multi-surface display device according to claim 1, wherein the display panel is a liquid crystal display panel, an organic light-emitting diode display panel or an electronic paper display panel.

10. The annular multi-surface display device according to claim 9, wherein the display panel is a touch display panel.

11. The annular multi-surface display device according to claim 1, further comprising: a camera device, a sliding slot disposed on an inner surface of the display panel that is opposite to the outer surface of the display panel, a support member for supporting a rotation of the camera device or a sliding of the camera device along the sliding slot, and a control chip for controlling movement of the support member to enable the camera device to capture images outside the display panel.

12. The annular multi-surface display device according to claim 11, wherein the sliding slot spirally ascends along the inner surface of the closed annular structure.

13. The annular multi-surface display device according to claim 6, wherein the transparent prism structure covers the sealing area of the two opposite sides as well as part of areas that surround the sealing area.

14. The annular multi-surface display device according to claim 1, wherein along a direction perpendicular to the two opposite sides, a cross section of the outer surface which forms the tubular surface is of a circular shape or an oval shape.

15. The annular multi-surface display device according to claim 1, wherein the two opposite sides of the display panel are sealed together through an approach of pressing together grooves and corresponding projections that match each other, an approach of gluing the two sides together, an approach of using screws to connect the two sides together, or an approach of using a sealing board to seal the two sides together.

16. The annular multi-surface display device according to claim 1, wherein the display panel is frameless at least on the sealing area.

17. The annular multi-surface display device according to claim 1, wherein the display panel further comprises a circuit board, the circuit board and the display panel are connected with each other through a flexible electronic skin.

18. The annular multi-surface display device according to claim 1, wherein the display panel is a liquid crystal display panel, an organic light-emitting diode display panel or an electronic paper display panel.

* * * * *